United States Patent [19]
Smith, Jr.

[11] Patent Number: 5,446,223
[45] Date of Patent: Aug. 29, 1995

[54] ALKYLATION OF ORGANIC AROMATIC COMPOUNDS

[75] Inventor: Lawrence A. Smith, Jr., Houston, Tex.

[73] Assignee: Chemical Research & Licensing Company, Pasadena, Tex.

[21] Appl. No.: 247,896

[22] Filed: May 23, 1994

[51] Int. Cl.$^6$ .......................... C07C 1/00; C07C 2/64
[52] U.S. Cl. .................... 585/313; 585/316; 585/323; 585/449; 203/DIG. 6
[58] Field of Search ............... 585/313, 316, 323, 449; 203/DIG. 6

[56] References Cited

U.S. PATENT DOCUMENTS

| | | | |
|---|---|---|---|
| 3,531,539 | 9/1970 | Tidwell | 260/677 |
| 4,232,177 | 11/1980 | Smith, Jr. | 585/324 |
| 4,316,997 | 2/1982 | Vaughan | 385/458 |
| 4,317,949 | 3/1982 | Vaughan | 585/458 |
| 4,423,254 | 12/1983 | Olah | 568/781 |
| 4,443,559 | 4/1984 | Smith, Jr. | 502/527 |
| 4,446,329 | 5/1984 | Waller | 585/458 |
| 4,469,908 | 9/1984 | Burress | 585/467 |
| 4,570,027 | 2/1986 | Boucher et al. | 585/455 |
| 4,849,569 | 7/1989 | Smith, Jr. | 585/446 |
| 4,950,834 | 8/1990 | Arganbright et al. | 585/446 |
| 5,019,669 | 5/1991 | Adams et al. | 585/446 |
| 5,043,506 | 8/1991 | Crossland | 585/449 |
| 5,047,141 | 9/1991 | Chu | 208/120 |
| 5,082,990 | 1/1992 | Hsieh et al. | 585/467 |
| 5,086,193 | 2/1992 | Sy | 585/446 |
| 5,113,031 | 5/1992 | Sy | 585/467 |
| 5,157,180 | 10/1992 | West et al. | 585/449 |
| 5,215,725 | 6/1993 | Sy | 422/212 |
| 5,243,115 | 9/1993 | Smith, Jr. et al. | 585/446 |
| 5,262,576 | 11/1993 | Smith, Jr. | 585/447 |

OTHER PUBLICATIONS

Kirk-Othmer, *Encyclopedia of Chemical Technology*, 3rd Edition vol. 21, pp. 772–779 (year unavailable).

Primary Examiner—Anthony McFarlane
Assistant Examiner—Nhat D. Phan
Attorney, Agent, or Firm—Kenneth H. Johnson

[57] ABSTRACT

The aging rate of the catalyst in a process for the concurrent alkylation of aromatic with olefin and distillation of reaction components (reactants and products) in a distillation column reactor in a catalyst bed wherein the catalyst also serves as the distillation structure, is retarded by limiting the conversion of olefin in the catalyst bed to about 90 percent. A portion up to and including the entire unreacted aromatic and olefin in the overhead from the distillation column reactor are condensed and fed to a fixed bed alkylation reactor to substantially finish the conversion with a portion of the effluent from the fixed bed reactor recycled thereto to control the olefin content in the fixed bed reactor inlet to less than one volume percent, preferably less than 0.50 volume percent and thereby reduce the aging in that catalyst. A fixed bed transalkylation reactor is used to convert the polysubstituted alkylated aromatic products to mono-substituted alkylated aromatic products.

20 Claims, 2 Drawing Sheets

5,446,223

ALKYLATION OF ORGANIC AROMATIC COMPOUNDS

BACKGROUND OF THE INVENTION

1. Field of the Invention

The present invention relates to a process for the alkylation of organic aromatic compounds. More particularly the invention relates to a process for the concurrent alkylation and distillation of reaction components (reactants and products) in a catalyst bed wherein the catalyst also serves as the distillation structure.

2. Related Art

Ethyl benzene and cumene are currently produced by the reaction of benzene and the respective olefin, i.e., ethylene and propylene by acid catalysis. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes. Advantages of the present invention are that the catalyst are not highly corrosive and do not require periodic regeneration, the heat of reaction is used efficiently, only low volume of recycle is required and the feed ratios can approach unity.

Straight pass fixed bed acidic catalysts have been proposed and used for the alkylation of aromatic compounds. Burress in U.S. Pat. No. 4,469,908 and Young in U.S. Pat. No. 4,371,714 both suggest the use of zeolites as alkylation catalysts. Additionally Vaughan in U.S. Pat. No. 4,317,949 and Olah in U.S. Pat. No. 4,423,254 suggest the use of polyfluorosulfonic acids as alkylation catalysts.

Recently a new method of carrying out catalytic reactions has been developed, wherein the components of the reaction system are concurrently separable by distillation, using the catalyst structures as the distillation structures. Such systems are described variously in U.S. Pat. Nos. 4,215,011; 4,232,177; 4,242,530; 4,250,052; 4,302,356; and 4,307,254 commonly assigned herewith. Commonly assigned U.S. Pat. No. 4,849,569 discloses the use of this system in aromatic alkylations. Briefly, a structure described in the patents is a cloth belt with a plurality of pockets spaced along the belt, which is then wound in a helix about a spacing material such as stainless steel knitted mesh. These units are then disposed in the distillation column reactor.

In addition, commonly assigned U.S. Pat. No. 4,443,559 discloses a variety of catalyst structures for this use and is incorporated herein.

SUMMARY OF THE INVENTION

Briefly, the present invention is a process for the alkylation of organic aromatic compounds with olefin by contacting the aromatic compound with the olefin in a distillation column reactor containing a fixed bed acidic catalytic distillation structure in a distillation reaction zone thereby catalytically reacting said aromatic compound and said olefin to produce a first alkylated aromatic product; concurrently in said fixed bed fractionating the resultant first alkylated aromatic product from the unreacted materials; recovering unreacted materials comprising olefin and aromatic compound; partially condensing the unreacted olefin and aromatic compound from the fractionation under conditions to primarily condense the aromatic compound; removing of a portion of the unreacted olefin; feeding the remaining unreacted olefin and aromatic compound under conditions of reaction to a straight pass fixed bed acidic catalyst to form a second alkylated aromatic product; recycling a portion of the second alkylated aromatic product to said straight pass fixed bed acidic catalyst in admixture with the unreacted olefin and aromatic compound before feeding to said straight pass fixed bed catalyst, the amount of said recycled second alkylated aromatic product being determined such that the total olefin concentration in the combined feed to said straight pass fixed bed is less than 1 vol %, preferably less than 0.50 vol percent. This process results in a very high conversion of the olefin. By recovering the olefin removed from the unreacted olefin/aromatic compound mixture and returning it to the olefin feed to the distillation reaction zone (first alkylation) an essentially 100% conversion of the olefin may be obtained.

The alkylated aromatic product comprises mono- and polyalkylated aromatic compounds. In the exemplified reaction the principal alkylated benzene product is ethyl benzene. In addition there are other alkylated products including di- and trace quantities of toluene, xylenes, butyl benzenes and cumene, which are believed to be disproportion and isomerization products of ethyl benzene.

In a preferred process the monoalkylated aromatic is separated from the total alkylated aromatic product and the residual alkylated products remaining after the monoalkylated aromatic separation are passed to a transalkylation reactor operated under conditions to transalkylate polyalkylated aromatics to monoalkylates, e.g., diethyl benzene and triethyl to ethyl benzene, which is separated from the other materials in transalkylation product stream and may be combined with the monoalkylated aromatic from first separation.

DETAILED DESCRIPTION OF THE INVENTION

Figure 1:
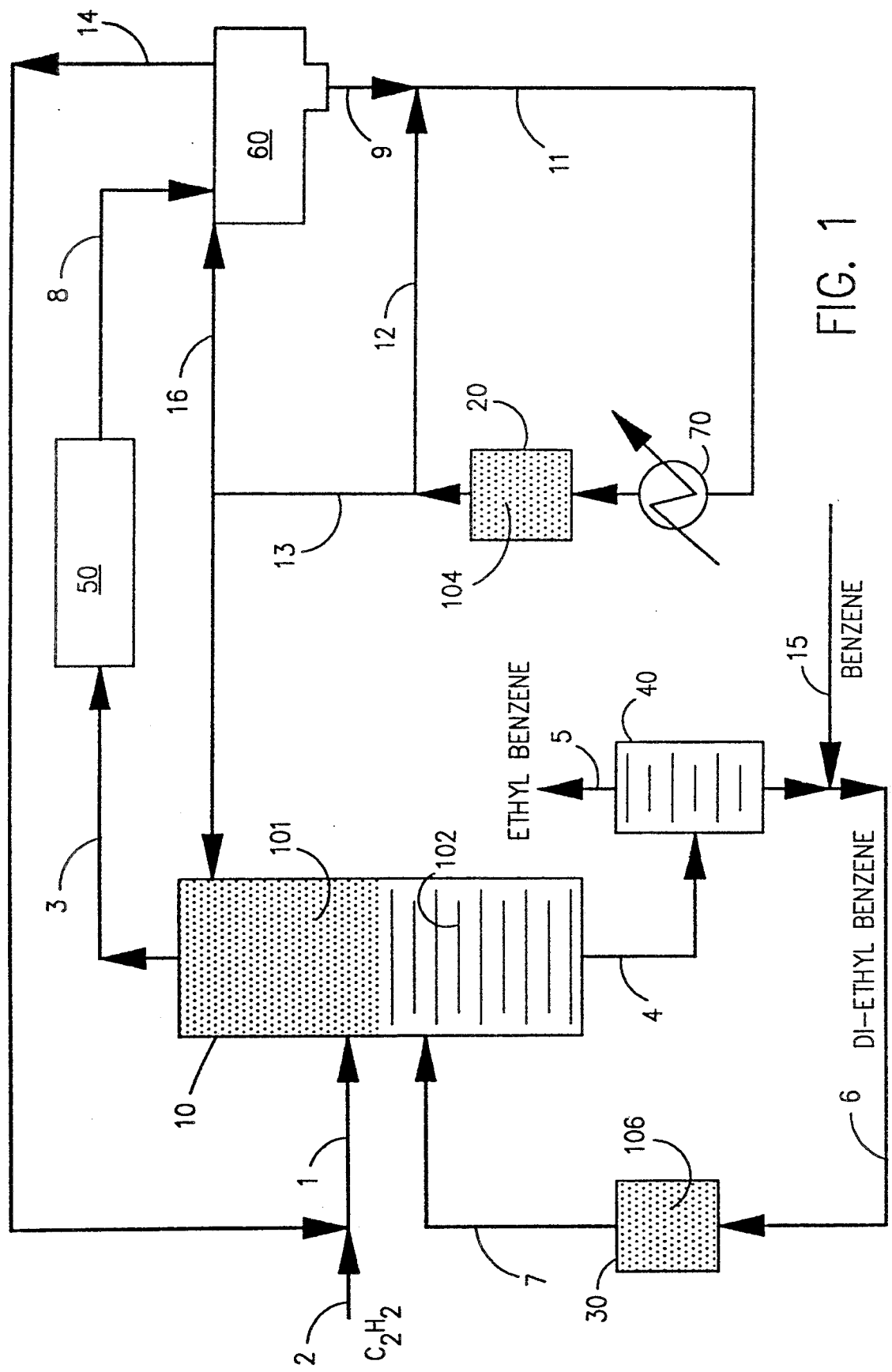
FIG. 1 is a flow diagram in schematic form of one embodiment of the present invention wherein less than the entire unreacted overhead is condensed.

The present invention is exemplified by the preparation of ethyl benzene by contacting the benzene with ethylene in a distillation column reactor containing a fixed bed acidic catalytic distillation structure.

In a preferred process the residual alkylated products remaining after ethyl benzene (monoalkylated aromatic) separation are passed to a transalkylation reactor operated under conditions to transalkylate polyalkylated benzene, e.g., diethyl benzene and triethyl to ethyl benzene, which is separated from the other materials in transalkylation product stream and may be combined with the ethyl benzene from first separation. Alternatively the two ethyl benzene containing streams may be combined and the ethyl benzene separated therefrom with the residual stream or a portion thereof being the feed to the transalkylation reactor. The principal residual alkylated product is diethyl benzene.

The transalkylation reactor may be operated as a straight pass reactor. The transalkylation is preferably carried out in liquid phase using a mole sieve catalyst. The transalkylated product contains a substantial concentration of ethyl benzene which may be recovered by fractional distillation, for example and combined with the ethyl benzene recovered from the alkylation product or the two streams may be combined for recovery of ethyl benzene.

The catalytic distillation structure provides both the catalytic sites and the distillation sites. The alkylated benzene product is withdrawn from the distillation column reactor at a point below the fixed bed and unreacted organic aromatic compound may be taken off as an overhead. Preferred acidic catalysts are molecular sieves (mole sieves).

More specifically the mole sieve catalyst packing is of such a nature as to allow vapor flow through the bed, yet provide a sufficient surface area for catalytic contact as described in the previously noted U.S. Pat. No. 4,443,559, and U.S. Pat. Nos. 4,215,011 and 4,302,356 which are incorporated herein in their entirety. The catalyst packing is preferably arranged in the upper portion of the distillation column reactor, more preferably occupying about one-third to one half of the column and extending substantially to the upper end thereof.

The olefin (e.g., ethylene) feed to the reaction is preferably made below the catalyst bed thereby allowing mixing of the reactants before contact with the catalyst bed. In another embodiment the olefin feed to the reaction is preferably made into the catalyst bed, such as between the bottom of the fixed bed, and the upper one-fourth section thereof preferably in the middle one-half of the bed.

The benzene feed may be added at any point in the reactor, for example it may be added to the fixed bed, the transalkylator or to the reflux as makeup. In the operation of the transalkylator a sufficient quantity of benzene is required to allow the reaction to proceed. The benzene may be added to the feed to the transalkylator along with the residual from the ethyl benzene separation.

Also, in order to achieve high selectivity toward monosubstitution (which is a preferred aspect of the present invention), there is a large excess of the organic aromatic compound to the olefin in the reactor in the range of 2 to 100 moles of benzene per mole of olefin, that is, the net molar feed ratio of aromatic organic compound: olefin may be close to 1:1, although the system is operated so as to maintain a substantial molar excess of organic aromatic compound to olefin in the reaction zone. In the event the make up benzene for the transalkylation is to be derived from the overhead/reflux stream of the alkylation reactor the feed molar ratio of the benzene: ethylene may exceed 1:1, e.g. 1.1–2:1.

The alkylated product is the highest boiling material and is separated in the lower portion of the column usually as bottoms. The aromatic compound, e.g. benzene, is usually the second highest boiling component (excluding inerts) as noted above, however, by operating with a large excess of benzene and a sufficient height of catalyst packing in the reactor, the major portion of the olefin (about 90 percent) is reacted, thereby reducing the separation and recovery problems. The success of catalytic distillation lies in an understanding of the principles associated with distillation. First, because the reaction is occurring concurrently with distillation, the initial reaction product is removed from the reaction zone quickly as it is formed. The removal of the alkylation product minimizes polysubstitution and decomposition of the alkylation product. Second, because the organic aromatic compound is boiling, the temperature of the reaction is controlled by the boiling point of that component at the system pressure. The heat of the reaction simply creates more boil up, but no increase in temperature. Third, the reaction has an increased driving force because the reaction products have been removed and cannot contribute to a reverse reaction (Le Chatelier's Principle).

As a result, a great deal of control over the rate of reaction and distribution of products can be achieved by regulating the system pressure. Also, adjusting the through-put (residence time=liquid hourly space velocity$^{-1}$) gives further control of product distribution and degree of olefin conversion. The temperature in the reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus controlled by the pressure; by increasing the pressure, the temperature in the system is increased, and vice versa. It can also be appreciated that in catalytic distillation as in any distillation there is both a liquid phase (internal reflux) and a vapor phase. Thus, the reactants are partially in liquid phase which allows for a more dense concentration of molecules for reaction, whereas, the concurrent fractionation separates product and unreacted materials, providing the benefits of a liquid phase system (and a vapor phase system) while avoiding the detriment of having all of the components of the reaction system continually in contact with the catalyst which would limit the conversion to the equilibrium of the reaction system components.

The overheads from the distillation column reactor are partially condensed to separate the unreacted benzene from the unreacted ethylene. The partially condensed overheads are passed to an accumulator where benzene, saturated with ethylene, is collected and the gaseous ethylene taken off. The saturated benzene is fed to a straight pass fixed bed alkylation reactor where essentially all of the olefins contained therein react with the benzene to produce additional alkylated product. A portion of the effluent from the straight pass fixed bed reactor is recycled to the reactor inlet to control the ethylene content at the reactor inlet to less than one percent, preferably less than 0.50 percent. The low ethylene content has been found to enhance the life of the catalyst in the polishing reactor. The gaseous ethylene may then be recycled back to the distillation column reactor.

CATALYSTS

The preferred catalysts for the reactions are acidic molecular sieves. Molecular sieves are porous crystalline, three-dimensional alumina-silicates of the zeolite mineral group. The crystal skeleton is composed of silicon and aluminum atoms each surrounded by four oxygen atoms to form a small pyramid or tetrahedron (tetrahedral coordination). The term molecular sieve can be applied to both naturally occurring zeolites and synthetic zeolites. Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Usually synthetic zeolites are prepared in the sodium form, that is, with a sodium cation in close proximity to each aluminum tetrahedron and balancing its charge. To date seven principal types of molecular sieves have been reported, A, X, Y, L, erionite, omega and mordenite. The A type have relative small pore size. By the term pore size is meant the effective pore size (diameter) rather than the free pore size (diameter). Types X and Y have larger pore size (approximately 10 Å.) and differ as to the range of ratio of $Al_2O_3$ to $SiO_2$ as:

Type X - - - $Al_2O_3/2.0-3.0$ $SiO_2$
Type Y - - - $Al_2O_3/3.0-6.0$ $SiO_2$
Type L and other types listed above have still higher ratios of $SiO_2$ to $Al_2O_3$ The mole sieve catalysts employed in the present invention are the acid form mole sieves or exhibit acidic characteristics. The acid form of the mole sieves is commercially available, but also may be prepared by treating the mole sieves with acid to exchange Na for hydrogen. Another method to produce the acid form is to treat the mole sieve with decomposable cations (generally ammonium ions) to replace Na with the decomposable ions and thereafter to heat the mole sieve to decompose the cation, leaving the acid form. Generally the Na form mole sieve is treated with soluble ammonium salts to remove the Na and thereafter the mole sieve is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Mole sieves, which have had their alkali metal reduced to low levels by partial treatment with $NH^+_4$ and partial multivalent metal cation exchange, possess increased activity and increased stability.

In addition to mole sieves which are acidic according to the Brönsted Theory those mole sieves which exhibit acidic characteristics under the Lewis Theory, for example, calcium exchanged mole sieves are suitable for the present reaction. By exchanging the univalent cations (e.g. $Na^+$) with multivalent cation, strong ionic activity is imparted. The ratio of $SiO_2$: $Al_2O_3$, valence and radius of the cation and the extent of exchange all affect the catalyst activity. In general activity increases with (1) increased $SiO_2$ $Al_2O_3$ ratio, (2) decreased cation radius and an increase in cation valence. The effect of replacing univalent ions (e.g. $Na^+$) with bivalent (e.g. $Ca^{++}$) is much greater than replacing the bivalent ions with cations of greater valence.

The various types of mole sieves having reduced alkali metal content are characterized as the acid form molecular sieve and are all contemplated as useful in the present invention.

It would appear that the pore size within the crystal lattice may affect the selectivity. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to the site can be altered by altering the structure of the crystal.

The acid form mole sieves are generally produced and available as particles in the range of <10 micron (powders) to 0.2 inch in diameter (beads).

In this form the mole sieves form too compact a bed and will not function adequately in a distillation, since there is a very large pressure drop through the bed and the free flow of internal reflux and rising vapor is impeded. Thus, mole sieves in the shape of conventional distillation structures, such as rings, saddles, and the like may be used in the distillation column reactor of the present invention. The particulate mole sieves may also be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material used to make the container is such that the catalyst is retained therein and will not pass through the openings in the material. Particles of about 0.15 mm size or powders may be used and particles up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume % up to about 65 volume %. Thus desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire or an expanded aluminum. Other resilient components may be similar open mesh knitted polymeric filaments of nylon, teflon and the like. Other materials such as highly open structures foamed material, e.g., reticulated polyurethane foam (rigid or resilient) may be formed in place or applied around the catalyst component.

In the case of larger catalyst components such as from about ¼ inch to ½ pellets, spheres, pills and the like each such larger component may be individually intimately associated with or surrounded by the spacing component as described above. It is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the mole sieve particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen are useful, but fiber glass cloth or "Teflon" cloth are preferred.

In the following examples the catalyst packing consisted of bags in the form of a fiber glass cloth belt approximately six inches wide with narrow pockets approximately ¾ inch wide sewn across the belt. The pockets are spaced about ¼ inch apart. These pockets are filled with the catalyst particles to form approximately cylindrical containers, and the open ends are then sewn closed to confine the particles. This belt is then twisted into a helical form to fit inside the column. Twisted in with the belt is also a strip of an open mesh knitted stainless steel wire, which serves to separate the mole sieve filled cloth pockets and provide a passage for vapor flow.

The wire mesh provides the support for the catalyst (belt) and provides some degree of vapor passage through the catalyst particles, which otherwise form a very compact bed which has a high pressure drop. Thus, the down flowing liquid is in intimate contact with the rising vapors in the column. In commercial-scale operations, it is contemplated, catalyst packing would be made up of alternating layers of mole sieve filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing should be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the catalyst-filled belts turned at right angles in successive layers to improve liquid and vapor flow distribution.

The form of the molecular sieve catalyst used in the fixed bed reactors should be such that lends itself to proper flow distribution and reactant contact with minimum pressure drop. The LZ-Y82 and Y84 and Beta zeolites have all exhibited exhibited very good performance in the present reactions.

FEED STREAMS

While the invention is directed to the alkylation of organic aromatic compounds with olefins generally, the process is exemplified by the production of ethyl benzene by the alkylation of benzene with ethylene.

The ethylene feed is preferably as high a purity as possible and generally contains 5 to 99.9% ethylene with the balance being alkanes such as ethane, propane, butane and the like which are inerts in this process. The presence of other olefins in materials may be substantially detrimental to the production of high purity ethyl benzene if that is required. Preferably the ethylene feed to the distillation column reactor will contain less than 1.5% other olefinic material.

However, operating the reaction with far less than a stoichiometric amount of olefin in the reaction zone of the distillation column reactor, as described, will normally keep the olefin level in the bottoms low or entirely eliminated. There may be some olefin going overhead even with the large molar excess of the organic aromatic compound present in the reaction zone. In those instances the overhead may be condensed to remove a major portion of the organic aromatic compound and the olefin and inerts removed for further separation or use.

Similarly inerts such as the alkane of the particular olefin(s) which are often found in olefin streams will be a possible contaminant.

The mole ratio of organic aromatic compound to olefin in the distillation column reactor may be in the range of 2 to 100:1, preferably 2 to 50:1 and more desirably about 2 to 10:1. The greater the excess of organic aromatic compound the more the selectivity to the monosubstituted product is improved. Alkylation is forced to completion with essentially 90 percent of the olefins converted, since the simultaneous and concurrent fractionation and removal of the alkylation product from the distillation column reactor does not allow the products to contribute to the reverse reaction (Le Chatelier's Principle). However, very large molar excesses of organic aromatic compounds require a very high reflux ratio, and a low unit productivity.

PROCESS

The length of the catalyst bed, particularly that portion wherein the reactants are in contact and the major portion of the reaction occurs, depends on the reactants, location of the olefin feed and the acceptable unreacted olefin in the streams leaving the tower.

The present alkylation and transalkylation reactions can be carried out at sub-through super atmospheric pressure, e.g., 0.20 to 50 atmospheres. The temperature will vary depending on the reactants and product. Furthermore, the temperature in the distillation column reactor the column will be as in any distillation column, the highest temperature will be in the bottom and the temperature along the column will be the boiling point of the composition at that point in the column under the particular conditions of pressure. Moreover, the exothermic heat of reaction does not change the temperature in the column, but merely causes more boil up. However, the temperatures within the column with the above considerations in mind will generally be in the range of 50° C., e.g. 50° C. to 300° C. and more preferably in the range of about 80° C. to 250° C. at pressures of 0.5 to 30 atmospheres.

The exothermic heat of reaction in the straight pass fixed bed alkylation reactor is limited by the degree of reaction and recycle of reactor effluent. The effluent from the straight pass fixed bed reactor is recycled to the reactor inlet to limit the olefin content to less than one vol %, preferably less than 0.50 vol %. In this way the temperature rise across the fixed bed is limited to about 5.5° C. (10° F.).

Fig. 1 illustrates one embodiment of the present invention, for the production of ethyl benzene by alkylating benzene with ethylene where a portion of the unreacted overhead is condensed.

Referring to the drawing, distillation column/reactor 10 is divided into two sections. In the upper section the catalyst packing (catalytic distillation structures) 101 is positioned as described. Linde molecular sieve LZ-Y82 1/16" (Union Carbide Corp.) is deposited in the pockets of fiber glass belts and formed in to a helix with stainless steel mesh as described.

The reactor 10 is a four inch diameter pilot column 70 feet tall with 35 feet of the catalyst packing in the upper portion. The lower portion of the column is a conventional distillation column configuration (equivalent 50 trays). Benzene is conveniently added as makeup via 15. The benzene can also be added through a separate line (not shown). The ethylene is fed to the column via 1 and 2 at the lower point of the catalyst packing 101. The reaction is exothermic and initiated by contacting the two reactants in the catalyst packing. Ethyl benzene and diethyl benzene are the principal reaction products. Both of these products as well as other polyalkylates are higher boiling than benzene and ethylene and are recovered via 4 as a bottoms product. The feed of ethylene may be such that there is a molar excess of benzene in the reactor, such that the overhead 3 is primarily benzene, the ethylene having been about 90% converted Alternatively the benzene reflux may be increased to increase the ratio of benzene to ethylene in the reactor, while the feed ratios may be about 1 to 1. In addition to benzene, some ethylene and other lights go off overhead. The overhead is passed to condenser 50 which is operated to condense substantially all of the benzene which passes via 8 to accumulator 60. The lights exit accumulator 60 via 14.

After separation of the benzene and ethylene in the accumulator 50, the benzene is saturated by ethylene and still contains about 0.75% ethylene. This ethylene saturated benzene is withdrawn via line 9 and 11 and heated in heat exchanger 70 and fed to straight pass fixed bed alkylation reactor 20 containing a fixed bed 104 of Y82 mole sieve. The effluent from the straight pass fixed bed reactor 20 exits via line 13 and contains essentially only benzene and alkylated benzene. A portion of the effluent is recycled to the reactor 20 feed via 12 to limit the ethylene concentration to less than 0 75 vol % preferably less than 0.50 vol %. Alternatively the recycle may be made via line 16 into accumulator 60 to help maintain the liquid level therein. The remainder of the effluent is returned to the upper end of distillation column reactor 10 as reflux and to separate the alkylated product from unreacted benzene. The gaseous ethylene from the separator 60 is recycled back to ethylene feed line 2 via line 14.

The bottoms in reactor 10 contain a mixture of ethyl benzene and diethyl benzene which pass via 4 to splitter 40, which is a conventional distillation column operated to fractionate ethyl benzene and diethyl benzene. The ethyl benzene is recovered as overhead 5 and the diethyl benzene and other polyalkylates recovered as a bottoms product. In this preferred embodiment the diethyl benzene is sent via 6 to the transalkylator 30 containing the LZ-Y82 catalyst 106. This is a single or multiple straight pass fixed bed 106 through which the polyalkylated benzene and benzene added through line 15 pass at 140° to 210° C. under sufficient pressure to maintain the liquid phases at LHSV of 1 to 5.

However, in this preferred embodiment it is desired to maximize ethyl benzene production. There is an equilibrium between benzene and diethyl benzene in the catalyst in the transalkylator as:

Benzene+Diethyl Benzene→Ethyl benzene

There is substantially no ethylene in the transalkylator and a large volume of benzene along with the polyalkylated reaction products such as diethyl benzene, hence, the reversible reaction favors the production of ethyl benzene, which is being continuously removed from the catalytic zone as the stream passes through.

In the embodiment of Fig.1 this product stream 7 passes back to distillation column reactor 10 where the ethyl benzene is separated from the benzene which is used as reactant in catalyst bed 101. Since the effluent from the straight pass fixed bed reactor 104 contains both mono- and di- substituted benzene its return to the distillation column reactor 10 allows the alkylated benzene to be separated in the lower portion 102 along with the initial reaction products. These are passed along with the bottoms 4 to splitter 40 and transalkylator 30 as discussed above.

Figure 2:
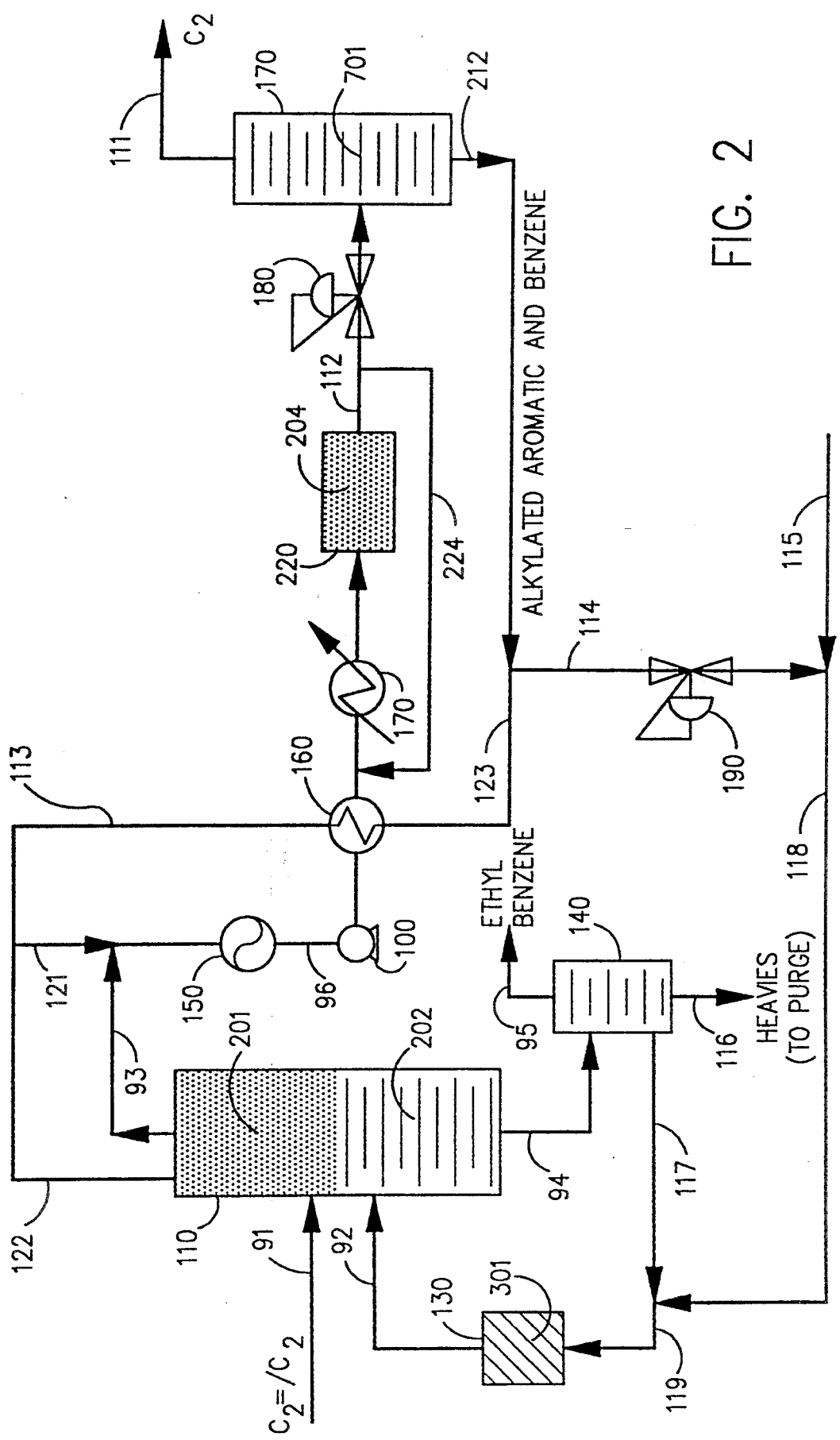
FIG. 2 is a flow diagram in schematic form of an embodiment of the present invention wherein the entire unreacted overhead is condensed.

Referring to FIG. 2, distillation column/reactor 110 is divided into two sections. In the upper section the catalyst packing (catalytic distillation structures) 201 is positioned as described. Linde molecular sieve LZ-Y82 1/16" (Union Carbide Corp.) is deposited in the pockets of fiber glass belts and formed in to a helix with stainless steel mesh as described.

The reactor 110 is a four inch diameter pilot column 70 feet tall with 35 feet of the catalyst packing in the upper portion. The lower portion of the column 202 is a conventional distillation column configuration (equivalent 50 trays). Benzene is conveniently added as makeup via 115 to transalkylator 301. The benzene can also be added through a separate line (not shown). The ethylene is fed to the column via 91 at the lower point of the catalyst packing 201. The reaction is exothermic and initiated by contacting the two reactants in the catalyst packing. Ethyl benzene and diethyl benzene are the principal reaction products. Both of these products as well as other polyalkylates are higher boiling than benzene and ethylene and are recovered via 94 as a bottoms product. The feed of ethylene may be such that there is a molar excess of benzene in the reactor, such that the overhead 93 is primarily benzene, the ethylene having been about 90% converted. Alternatively the benzene reflux may be increased to increase the ratio of benzene to ethylene in the reactor, while the feed ratios may be about 1 to 1. In addition to benzene, some ethylene and other lights go off overhead. The overhead is passed to condenser 150 where a substantial portion of the benzene is condensed hence via 96 to compressor 100 which is operated in conjunction with heat exchangers 160 and 170 to totally condense substantially all of the overheads before being fed to alkylation reactor 220 containing a straight pass fixed bed 204 of LZ-Y82 mole sieve catalyst.

The effluent from the straight pass fixed bed reactor exits via line 112 and contains ethyl benzene, di-ethyl benzene, unreacted benzene, and inert alkanes which are predominantly ethane. The effluent from the alkylation reactor 220 is passed to a standard distillation column 170 through back pressure valve 180 wherein the inerts are taken overhead as gas via line 111 and the ethyl benzene, di-ethyl benzene and benzene taken as liquid bottoms 212. A portion of the effluent from the straight pass fixed bed reactor 220 is recycled via 224 to the reactor 220 feed to limit the ethylene concentration to less than one vol %, preferably less than 0.50 vol %.

A portion of the liquid bottoms is returned to distillation column reactor 110 via lines 123, 113 and 122. Some of the liquid bottoms in line 113 may be recycled to the alkylation reactor feed via 121 to aid in reducing all of the overhead from reactor 110 to liquid phase for the straight pass fixed bed reactor 204. The remainder of the liquid bottoms is passed via lines 114 and 118 through back pressure valve 190 to a transalkylator reactor 130 as discussed below.

The bottoms in reactor 110 contain a mixture of ethyl benzene and diethyl benzene which pass via 94 to splitter 140, which is a conventional distillation column operated to fractionate ethyl benzene and diethyl benzene. The ethyl benzene is recovered as overhead 95 and the diethyl benzene and other polyalkylates recovered as a side draw 117. Any build up of .heavier ploy-substituted benzene may be periodically purged as bottoms via line 116. In this preferred embodiment the diethyl benzene is combined with the second fraction of liquid bottoms from fractionation column 170 and sent via lines 117 and 119 to the transalkylator 130 containing the LZ-Y82 catalyst 301. This is a single or multiple straight pass fixed bed 301 through which the polyalkylated benzene and benzene added through line 115 pass at 140° to 210° C. under sufficient pressure to maintain the liquid phases at LHSV of 1 to 5.

However, in this preferred embodiment it is desired to maximize ethyl benzene production. There is an equilibrium between benzene and diethyl benzene in the catalyst in the transalkylator as:

Benzene+Diethyl Benzene→Ethyl benzene

There is substantially no ethylene in the transalkylator and a large volume of benzene along with the polyalkylated reaction products such as diethyl benzene, hence, the reversible reaction favors the production of ethyl benzene, which is being continuously removed from the catalytic zone as the stream passes through.

In the embodiment of FIG.2 this product stream 92 passes back to distillation column reactor 110 where the ethyl benzene is separated from the benzene which is used as reactant in catalyst bed 201. Since the effluent from the straight pass fixed bed reactor 204 contains both mono- and di- substituted benzene its return to the distillation column reactor 110 allows the alkylated benzene to be separated in the lower portion 202 along with the initial reaction products. These are passed along with the bottoms 94 to splitter 140 and transalkylator 130 as discussed above.

The invention claimed is:

1. A process for the alkylation of organic aromatic compounds, comprising the steps of:
   (a) feeding a stream containing organic aromatic compounds and olefins to a distillation column reactor;
   (b) concurrently in said distillation column reactor:
      (1) contacting said stream with a particulate acidic catalyst whereby a portion of said organic aromatic compounds react with a portion of said olefins to form a reaction mixture containing a first alkylated aromatic product, unreacted organic aromatic compounds and unreacted olefins, and
      (2) separating by fractional distillation said first alkylated aromatic product from said unreacted organic aromatic compounds and from said unreacted olefins;
   (c) withdrawing said first alkylated aromatic product from said distillation column reactor as bottoms;
   (d) withdrawing said unreacted organic aromatic compounds and said unreacted olefins from said distillation column reactor as overheads;
   (e) condensing a portion of said overheads to separate said unreacted organic aromatic compounds from said unreacted olefins, said separated organic aromatic compounds being saturated with unreacted olefins;
   (f) feeding said olefin-saturated organic compounds to a straight pass alkylation reactor containing a fixed bed of particulate acidic catalyst wherein a portion of said unreacted organic aromatic compounds reacts with a portion of said olefins contained therein to form a reactor effluent containing a second alkylated aromatic product, unreacted organic aromatic compounds and unreacted olefins; and
   (g) recycling a portion of said effluent to said straight pass alkylation reactor such that the total olefin content entering the straight pass alkylation reactor is less than one volume percent.

2. The process according to claim 1 wherein said first alkylated aromatic product contains mono- and di-substituted aromatic compounds and further comprising the steps of:
   (h) fractionating said bottoms of step (c) to separate said mono- from said di-substituted aromatic compounds; and
   (i) feeding said di-substituted aromatic product along with additional organic aromatic compounds to a transalkylation reactor wherein a portion of said di-substituted aromatic compounds react with a portion of said additional organic aromatic compounds to produce a transalkylation effluent containing additional mono- substituted aromatic compounds.

3. The process according to claim 2 wherein the transalkylation effluent is fed to said distillation column reactor as reflux.

4. The process according to claim 3 wherein said second alkylated aromatic product contains mono- and di-substituted aromatic compounds and that portion of said effluent not recycled is fed to said distillation column reactor wherein said second alkylated aromatic product is removed as the bottoms of the distillation column reactor.

5. The process according to claim 1 wherein said separated unreacted olefins of step (e) are recycled to said distillation column reactor.

6. The process according to claim 1 wherein the particulate acidic catalyst in said distillation column reactor and said straight pass alkylation reactor are the same.

7. The process according to claim 6 wherein said particulate acidic catalyst is an acidic molecular sieve.

8. The process according to claim 1 wherein said organic aromatic compounds comprise benzene and said olefins comprise ethylene, propylene or a mixture thereof.

9. The process according to claim 8 wherein said first alkylated aromatic product comprises ethyl benzene and di-ethyl benzene and further comprising the steps of:
   (h) fractionating said bottoms to separate said ethyl benzene from said di-ethyl benzene; and (i) feeding said di-ethyl benzene along with additional benzene to a transalkylation reactor wherein a portion of said di-ethyl benzene aromatic compounds react with a portion of said additional benzene to produce a transalkylation effluent containing additional ethyl benzene.

10. The process according to claim 9 wherein the transalkylation effluent is fed to said distillation column reactor.

11. The process according to claim 10 wherein said second alkylated aromatic product contains ethyl benzene and di-ethyl benzene and that portion of said effluent not recycled is fed to said distillation column reactor wherein said second alkylated aromatic product is removed as the bottoms of the distillation column reactor.

12. The process according to claim 9 wherein said separated unreacted olefins of step (e) are recycled to said distillation column reactor.

13. The process according to claim 8 wherein said olefins comprise propylene.

14. The process according to claim 1 wherein substantially the entire unreacted overhead in step (e) is condensed.

15. The process according to claim 1 wherein the olefin content in the feed to the straight pass alkylation reactor is less than 0.75 vol. %.

16. A process for the alkylation of organic aromatic compounds with olefin by contacting said aromatic compound and olefin in a distillation column reactor containing a fixed bed acidic catalytic distillation structure in a distillation reaction zone thereby catalytically reacting said aromatic compound and said olefin to produce a first alkylated aromatic product; concurrently in said fixed bed fractionating the resultant first alkylated aromatic product from unreacted materials; recovering unreacted materials comprising said olefin and said aromatic compound; partially condensing the unreacted olefin and aromatic compound from the fractionating under conditions to primarily condense the aromatic compound; removing a portion of the unreacted olefin; feeding the remaining unreacted olefin and aromatic compound under conditions of reaction to a straight pass alkylation reactor containing a fixed bed acidic catalyst to form a second alkylated aromatic product; recycling a portion of the second alkylated aromatic product to said straight pass alkylation reactor in admixture with the unreacted olefin and aromatic compound before feeding to said straight pass alkylation reactor, the amount of said recycled second alkylated aromatic product being determined such that the total olefin concentration in the combined feed to said straight pass alkylation reactor is less than 1 vol %.

17. The process according to claim 16 wherein the combined feed to said straight pass alkylation reactor is less than 0.75 vol.% olefin.

18. The process according to claim 16 wherein the combined feed to said straight pass alkylation reactor is less than 0.50 vol. % olefin.

19. A process for the alkylation of organic aromatic compounds comprising:
(a) feeding a stream containing organic aromatic compounds and olefins to a straight pass alkylation reactor containing a fixed bed acidic catalyst wherein a portion of the organic aromatic compound reacts with at least a portion of the olefin compound to produce reactor effluent containing an alkylated aromatic product;
(b) withdrawing the reactor effluent from the reactor; and
(c) recycling and combining a portion of said entire effluent with said stream before feeding to said reactor, the amount of said recycled effluent being determined such that the total olefin concentration in the combined feed to said reactor is less than 0.75 vol %.

20. The process according to claim 19 wherein said effluent is divided into a first portion and a second portion, wherein said first and second portion have essentially the same composition.

* * * * *